(12) United States Patent
Silver et al.

(10) Patent No.: US 7,812,943 B2
(45) Date of Patent: Oct. 12, 2010

(54) ZEROETH ORDER IMAGING

(75) Inventors: Richard M. Silver, Darwood, MD (US); Ravikiran Attota, Germantown, MD (US); Robert Larrabee, Derwood, MD (US)

(73) Assignees: The United States of America as represented by the Secretary of Commerce, Washington, DC (US); The National Institute of Standards and Technology, Gaithersburg, MD (US)

( * ) Notice: Subject to any disclaimer, the term of this patent is extended or adjusted under 35 U.S.C. 154(b) by 172 days.

(21) Appl. No.: 11/926,418

(22) Filed: Oct. 29, 2007

(65) Prior Publication Data

US 2009/0109446 A1    Apr. 30, 2009

(51) Int. Cl.
*G01N 21/00* (2006.01)

(52) U.S. Cl. .................................... 356/237.5

(58) Field of Classification Search ............... 356/499, 356/512, 521, 237.4, 237.5
See application file for complete search history.

(56) References Cited

U.S. PATENT DOCUMENTS

| 7,576,911 B1 * | 8/2009 | Larimer .................... 359/385 |
| 2002/0101585 A1 * | 8/2002 | Benesch et al. .......... 356/237.4 |

* cited by examiner

*Primary Examiner*—Hwa S. A Lee
(74) *Attorney, Agent, or Firm*—Butzel Long

(57) ABSTRACT

A method of imaging critical dimensions by measuring the zeroeth order of diffracted light. The method involves providing a target, directing light onto the target so as to cause the target to diffract the light. The zeroeth order of the diffracted light is collected and analyzed to determine structural features of the target. The target can be an article of manufacture, such as a semiconductor device, or a separate target that is provided or fabricated on an article of manufacture. One of at least the wavelength and the angle at which the light is directed onto the target can be scanned. The target can fill all or only a portion of the field of view.

11 Claims, 11 Drawing Sheets

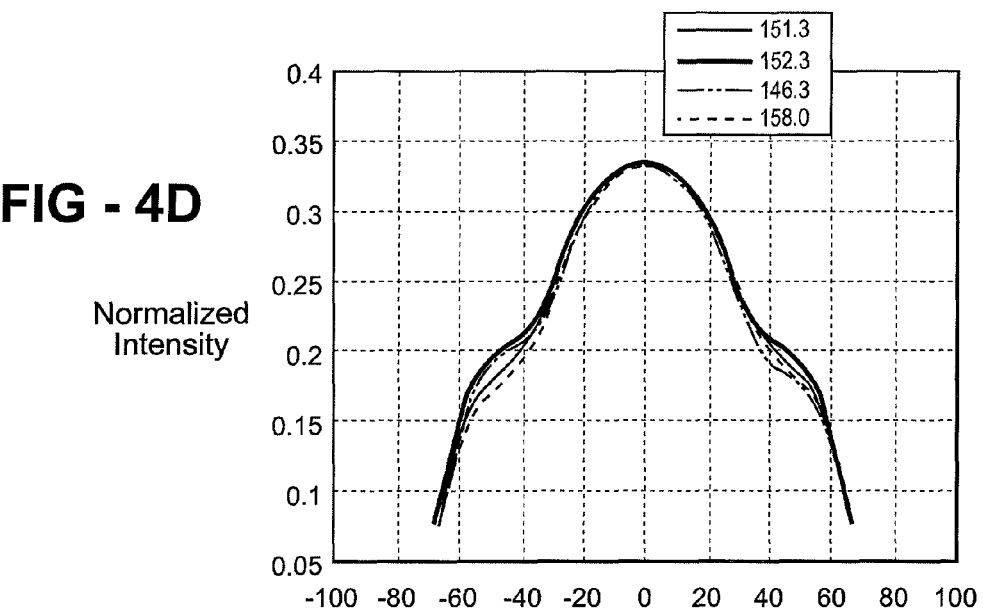
FIG - 4D
FIG - 5A
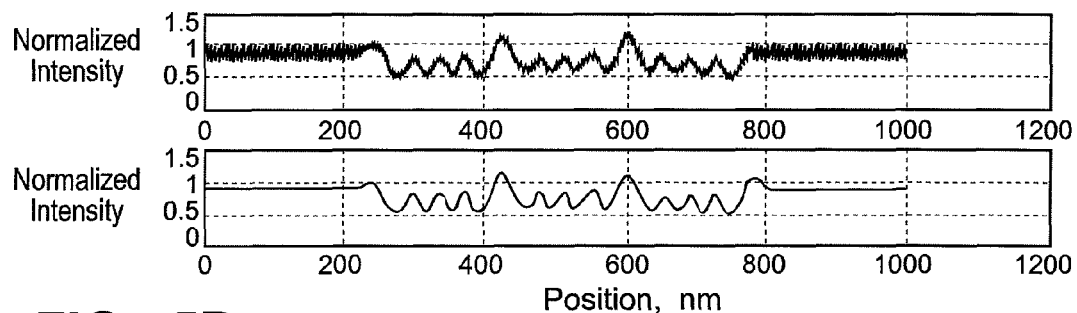
FIG - 5B
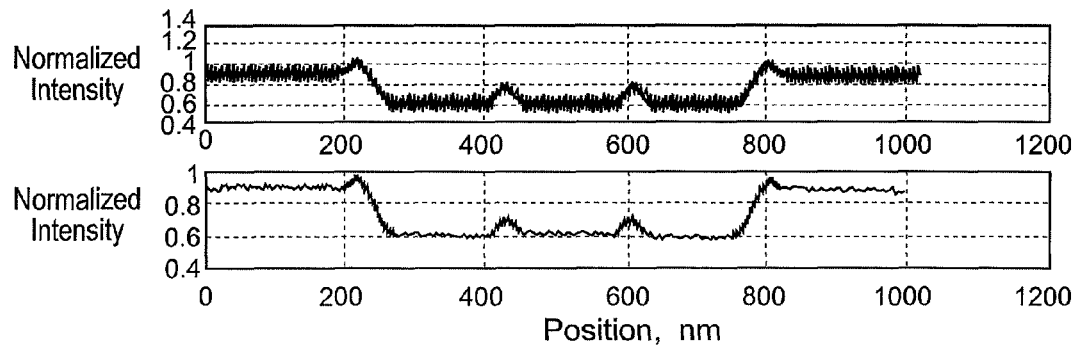

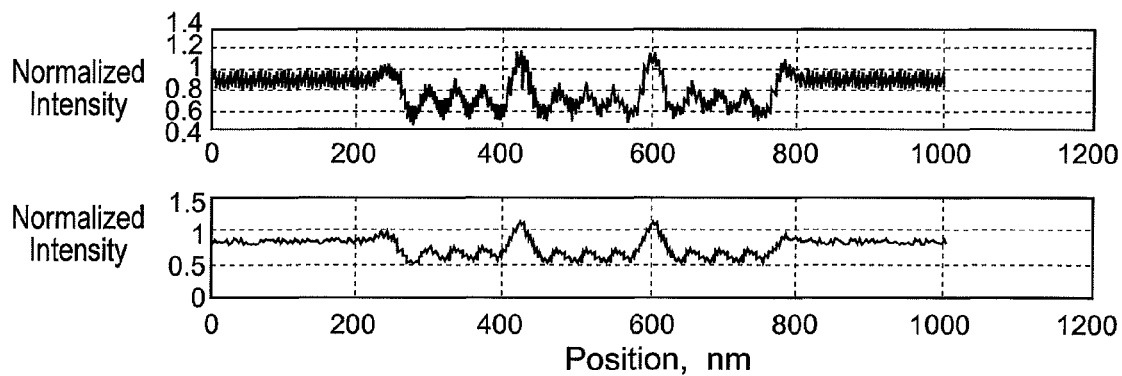
FIG - 5C
FIG - 6A
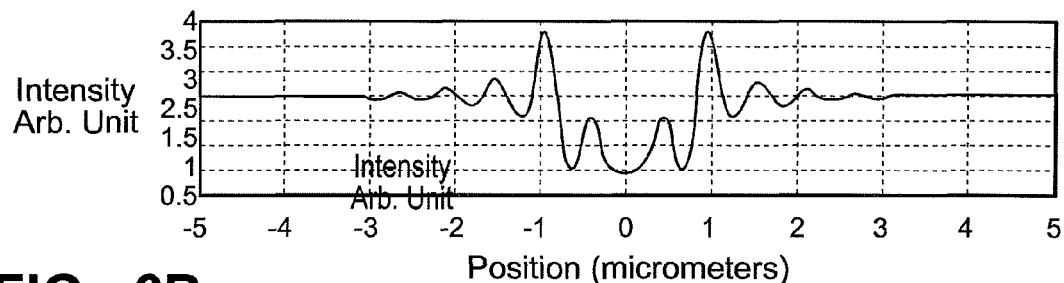
FIG - 6B
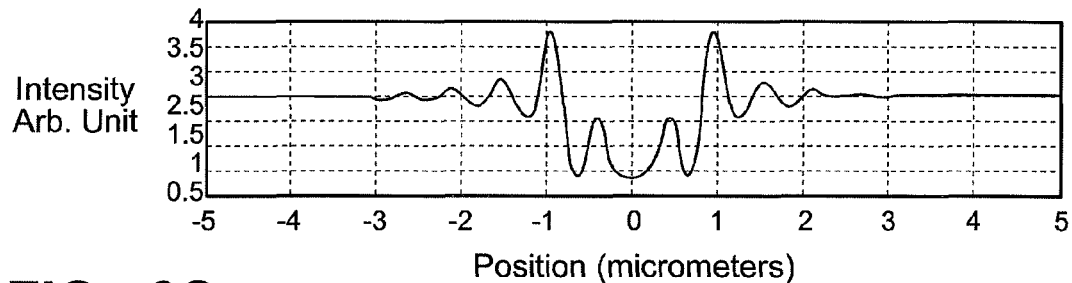
FIG - 6C
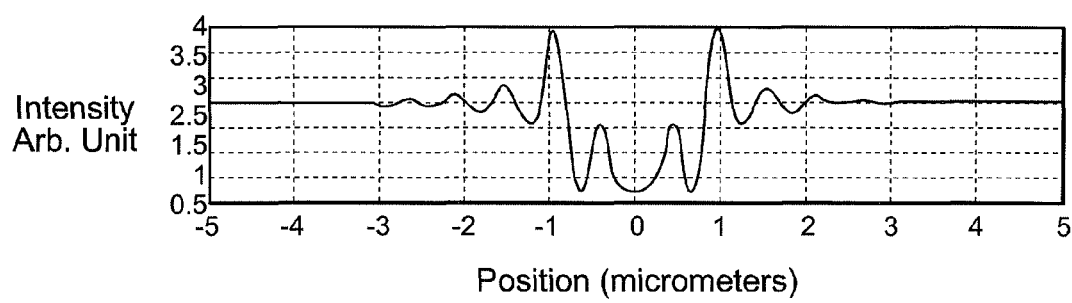

ZEROETH ORDER IMAGING

TECHNICAL FIELD

The present invention relates to high-resolution imaging and critical dimension (CD) metrology. More specifically the present invention is directed to imaging the zeroeth order of diffracted light from a target or article of manufacture and determining therefrom information of the structural features of the target or article of manufacture.

BACKGROUND ART

High-resolution imaging and metrology requirements in critical dimension (CD) metrology have largely rendered conventional optical image-based CD methods irrelevant for some time. The need to image features smaller than 90 nm, as is now routinely encountered in semiconductor manufacturing, has driven CD scanning electron microscopy (SEM) to the forefront for virtually all in-line or at-line CD metrology. Accurate CD SEM metrology has edge detection and modeling requirements at this scale and is faced with increasing high costs, throughput concerns and is generally not well suited to integrated metrology applications. In addition, there is recent work focused on evaluating electron beam induced line shrinkage or surface damage defects. As a result, there has been a recent shift in strategy to evaluate scatterometry as a manufacturing process control tool. Scatterometry has a high throughput, relatively low tool costs compared to an SEM, is less likely to cause target damage, and has shown excellent sensitivity and repeatability. Some of the drawbacks of scatterometry are the large target size requirements, a similar dependence on modeling, and potentially substantial dependence on underlying layers and optical properties.

The measurement requirements of overlay metrology are somewhat different than those encountered in CD metrology and more conventional optical tools continue to be the tool of choice. For the most part, overlay measurements are essentially pitch measurements between two layers and are well suited to image-based analyses which do not require modeling and an accurate estimation of a physical edge within a profile. To accomplish an overlay measurement with a scatterometry tool, modeling is fundamentally required. The challenges in using SEM for overlay are different than scatterometry as the SEM can make overlay measurements in an image-based mode. The challenges are more a result of imaging buried layers, such as imaging through photoresist, along with the increase cost and lower throughput. There has been some interests recently in evaluating SEM for use in overlay since there is a current push to design overlay targets which are composed of features that have device dimensions. Although the industry continues to use conventional optical tools for overlay metrology, there is a desire to evaluate different methods for use with device-sized overlay targets.

The importance of evaluating overlay with targets fabricated at device dimensions is known. One concern is that larger features used in overlay targets may not correctly reflect actual device overlay since the larger feature dimensions behave differently in the stepper optical systems and in subsequent process steps. In addition, overlay targets in the scribe area have always had some error with respect to overlay values in the active area. This concern has become more pronounced with the increased usage of step and scan procedure tools. The conventional scribe area targets do not capture some essential systematic errors which occur throughout the scanned field of view. Evaluations of small in-situ (in-chip) overlay targets and their potential utility and susceptibility to errors have been made. The measurement required of these small in-chip overlay targets and targets made of device sized features are responsible for much of the current development in high-resolution overlay imaging methods.

In parallel with high-resolution optical overlay development, scatterometry has recently drawn attention to its suitability and flexibility for implementation in integrated metrology applications. Optical tools can generally operate in an ambient environment and are well suited to integrated metrology applications. Although CD SEM tools have very good resolution and sensitivity, they are in general not well suited for use in integrated metrology applications such as built-in stepper track metrology capabilities. Several optical scatterometry tools have now been installed in stepper track systems where they operate in an ambient environment with additional complications introduced by the stepper track such as vibration and size limitations. With the growing importance of integrated metrology and tighter feed forward and feedback control, flexible metrology tools capable of operating in an air ambient with space limitations have become more important.

The present invention provides a method of imaging the structural features of a target or article of manufacture using the zeroeth order of diffracted light. The same method may be applied to higher order diffracted light.

DISCLOSURE OF THE INVENTION

According to various features, characteristics and embodiments of the present invention which will become apparent as the description thereof proceeds, the present invention provides a method of imaging the zeroeth order of diffracted light which involves the steps of;

a) providing a target;

b) directed light onto the target so as to cause the target to diffract the light;

c) collecting the zeroeth order of the diffracted light; and d) determining structural features of the target from the collected diffracted light.

The present invention further provides a method of imaging an article of manufacture which involves the steps of a) providing an article of manufacture having a target area thereon;

b) directed light onto article of manufacture so as to cause at least the target area to diffract the light;

c) collecting the zeroeth order of the diffracted light from the target area; and d) determining structural features of the target from the collected diffracted light from the target area.

BRIEF DESCRIPTION OF DRAWINGS

The present invention will be described with reference to the attached drawings which are given as non-limiting examples only, in which:

FIGS. 4A-4D show a complete set of experimental data and simulations results using electromagnetic scattering models for the case where the pitch is large and there is higher order diffraction.

FIGS. 5A-5C are images of an array of three small line arrays on a substrate.

FIGS. 6A-6F show the normal incidence 0° illumination image data which contains profiles for three different design CDs.

BEST MODE FOR CARRYING OUT THE INVENTION

The present invention is directed to high-resolution imaging and critical dimension (CD) metrology. More specifically the present invention is directed to imaging the zeroeth order of diffracted light from a target or article of manufacture and determining therefrom information of the structural features of the target or article of manufacture.

Conventionally an image takes multiple orders of diffracted light and forms an image in the image plane. If the structure however is too dense, that is the pitch of the grating is below the fundamental limit to capture the first order intensity, then only a constant intensity is captured by a large grating which fills the field of view. This is the typical situation encountered in scatterometry where a single wavelength of illumination is scattered off a target with a defined pitch. The diffracted light can be measured and with a scatterometer measuring only the zeroeth order, then a frequency or angle scan can yield a specific curve attributable to that diffraction grating. If the pitch of the grating is below the first order limit then only a zeroeth order profile can be obtained.

It is a key problem for imaging with optics as in bright field microscopy since the optical response is just a constant intensity profile if only zero order light is diffracted. Prior to the present invention an image of a large array which only diffracts or scatters the zeroeth order was generally thought to not yield useful information. However, if the intensity of the zeroeth order is accurately captured and normalized then a plot of the zeroeth order intensity versus angle of illumination or wavelength, according to the present invention provides a mapping with an optical microscope similar to a scatterometer. If the microscope is operated in a scatterfield type of mode where only selected "plane waves" (as approximated by the Scatterfield methodology) illuminate the sample, then the optical microscope can potentially measure the target linewidths and pitch.

Figure 1:
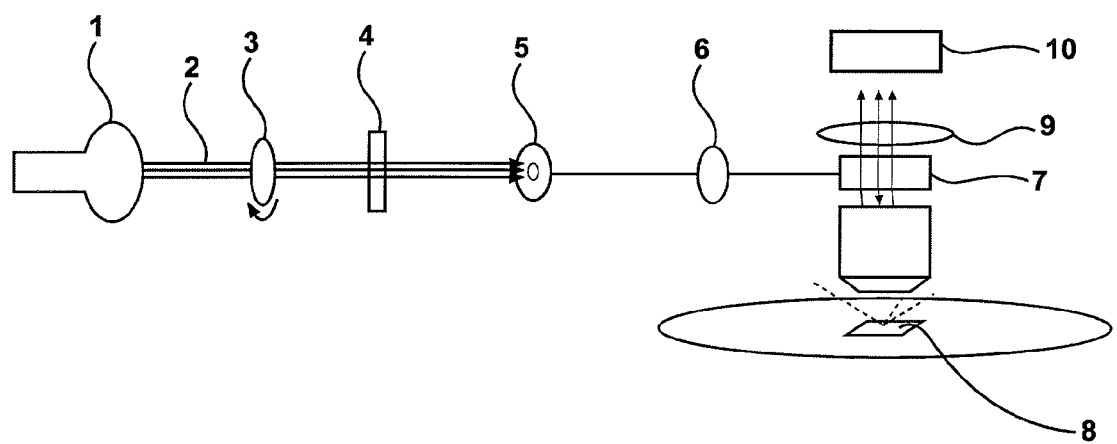
FIG. 1 is a schematic illustration of the optical configuration used according to one embodiment of the present invention.

FIG. 1 is a schematic illustration of the optical configuration used according to one embodiment of the present invention. As shown a light source 1 such as a standard fiber illuminator generates a beam of light 2 that passes through a polarizer 3 that can be rotated to select a desired polarity of light. The polarized light passes through a band pass filter 4 so that light of a desired wavelength is selected. The beam of light that is now of a selected wavelength passes through a small aperture 5, e.g. 200 micron, which can be scanned to select a desired illumination angle. The light which passes through aperture 5 is focused by lens 6 and strikes a beamsplitter 7. The beamsplitter directs a portion of the light onto the target 8 and directs the remaining and reflected light through a relay lens 9 and to an imaging device 10, such as a CCD camera.

FIGS. 2A-2D are experimental examples of date acquired according to one embodiment of the present invention. To acquire this data, the aperture 5 was scanned in the back focal plane across a large enough distance to clip the aperture at the extremes so that intensity falls off for positions in the back focal plane which correspond to angles of illumination greater than 60° as shown.

Figure 2A:
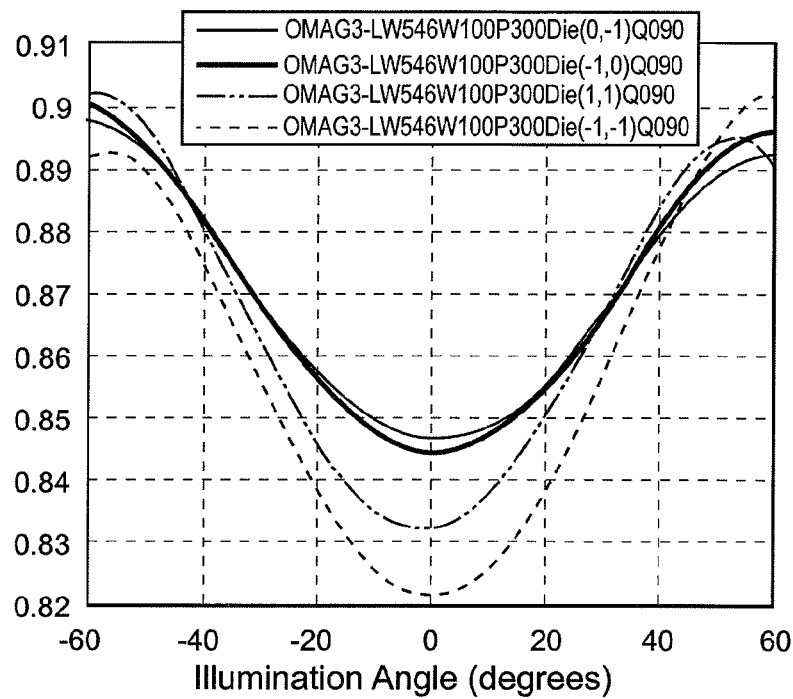
FIGS. 2A-2D are plots of the average integrated intensity plotted versus illumination angle as the angle of illumination is scanned.
Figure 2B:
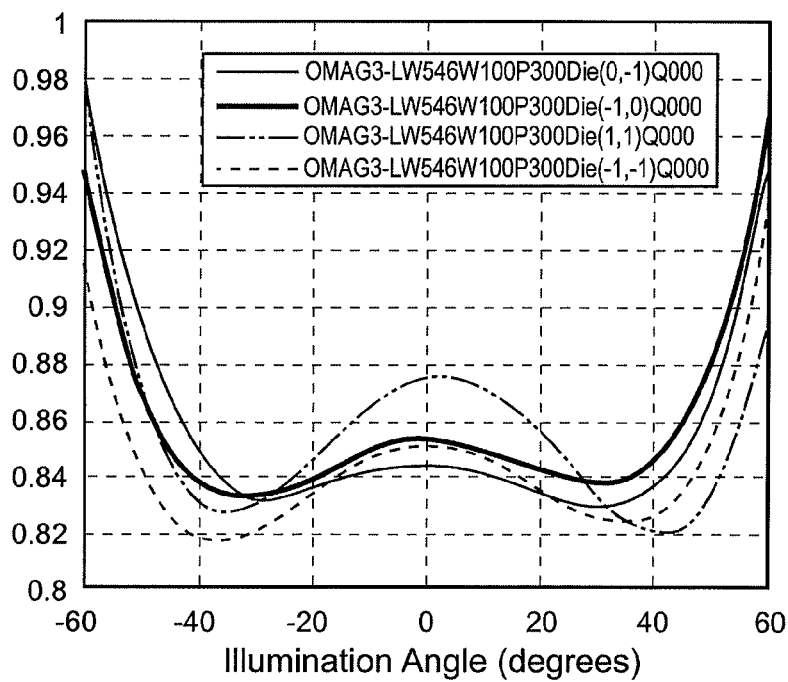
Figure 2C:
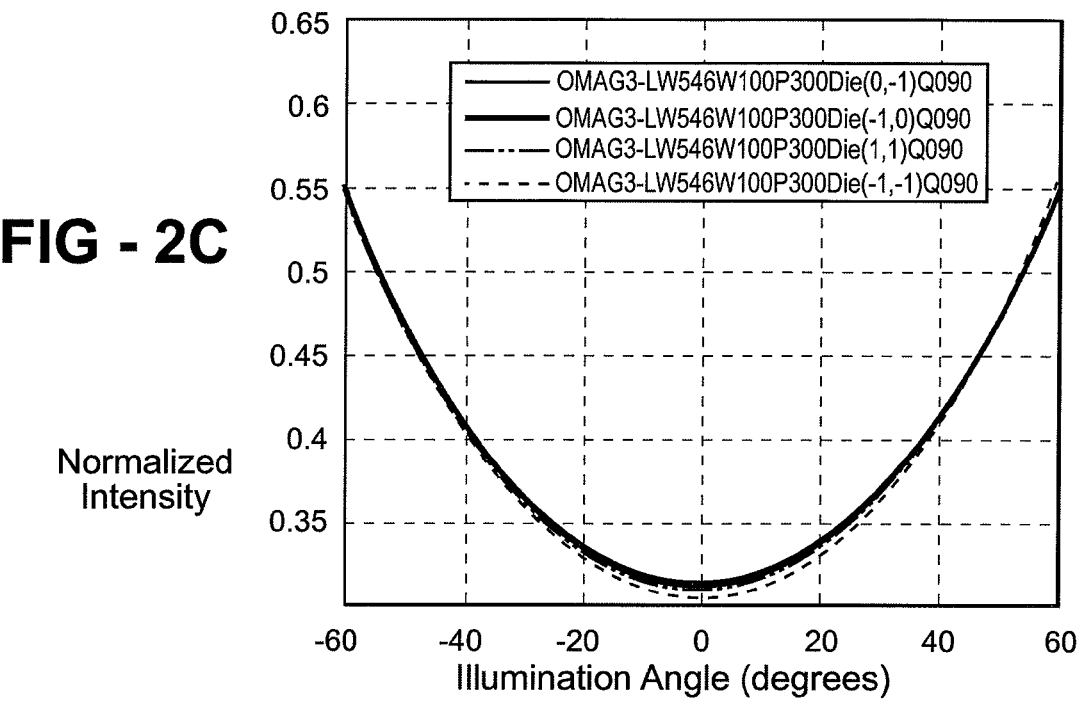
Figure 2D:
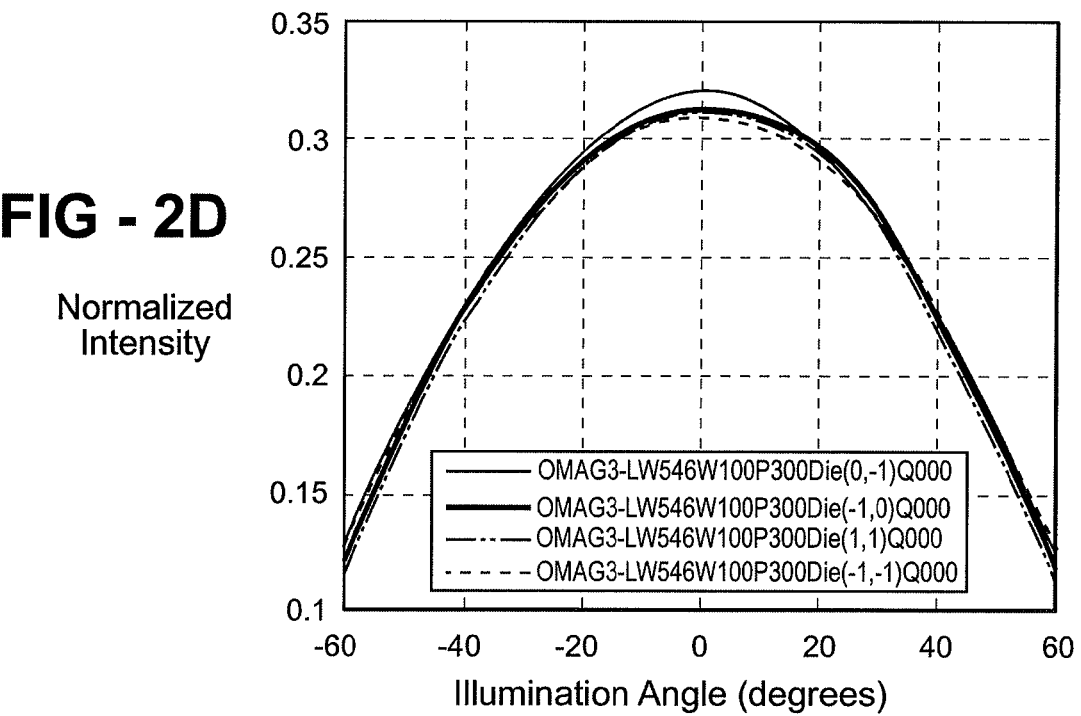

The data in FIGS. 2A-2D are plots of the average integrated intensity plotted versus illumination angle as the angle of illumination is scanned. FIG. 2A shows data for p polarization and FIG. 2B shows data for s polarization. FIGS. 2A-2D show a 300 nm pitch array with linewidths varying from 150 nm to 165.5 nm (Die 1, 1=156.5 nm, Die −1, 0=154 nm, Die 0. −1=150.6 nm and Die −1, −1=150 nm) based upon SEM values. The data shown in FIGS. 2A and 2B have not been normalized for silicon reflectivity (the substrate material) although they have been processed (normalized) for background and dark current compensation. The data shown in FIGS. 2C and 2D have been corrected for silicon reflectivity. This correction effectively scales the data, which in this case, increases the dynamic range in the graph, and makes the curves appear closer to each other in value relative to the raw uncorrected data.

The data in FIGS. 2A-2D shows good sensitivity to nm changes in linewidth. The images have been normalized to the background. A forth order fit was used to analyze the data. The dynamic range is in part the result of the background normalization. During the course of the present invention it was confirmed that this data is repeatable and shows a monotonic response to linewidth changes.

Figure 3A:
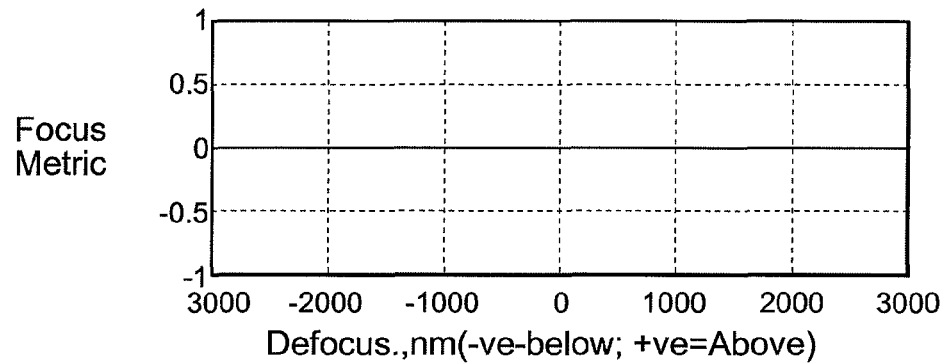
FIGS. 3A and 3B are focus metric profiles for dense (FIG. 3A) and non dense (FIG. 3B) images.

An array of lines, depending upon the illumination wavelength and period, exhibits two kinds of optical responses. It shows no contrast in the image if the period is small compared to the illumination wavelength (zero order optical response only) or higher order optical response can be present due to higher diffracted orders being captured in the optical system. The focus metric profiles from such examples are shown in FIGS. 3A (dense image) and 3B (not dense image).

Figure 3B:
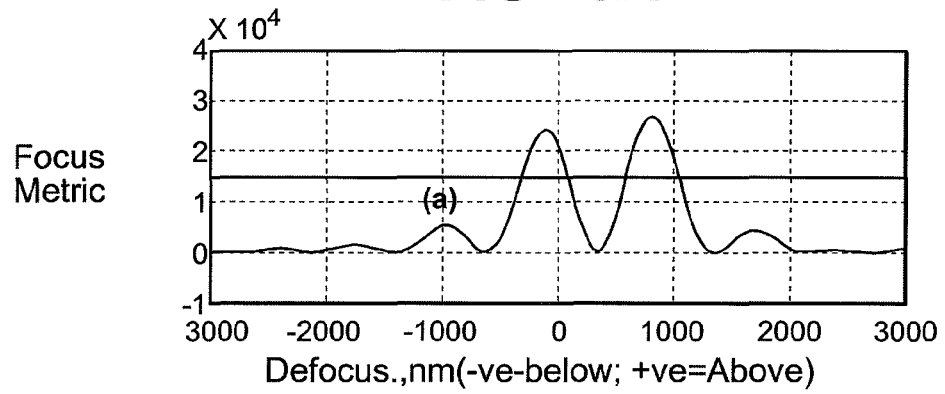

If the period is large, there is optical contrast as seen in FIG. 3B. The average integrated intensity can be captured again as a function of angle or wavelength for the example of higher order optical response as well.

FIGS. 4A-4D show a complete set of experimental data and simulations results using electromagnetic scattering models for the case where the pitch is large and there is higher order diffraction. The test samples used in FIGS. 4A-4D were 230 nm tall silicon lines with 600 nm pitch.

Figure 4A:
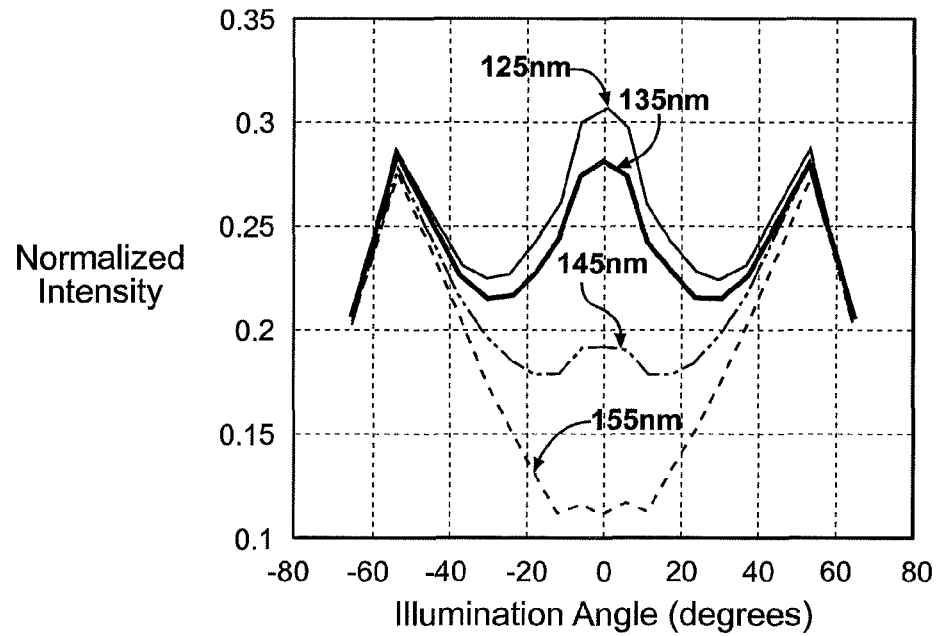
Figure 4B:
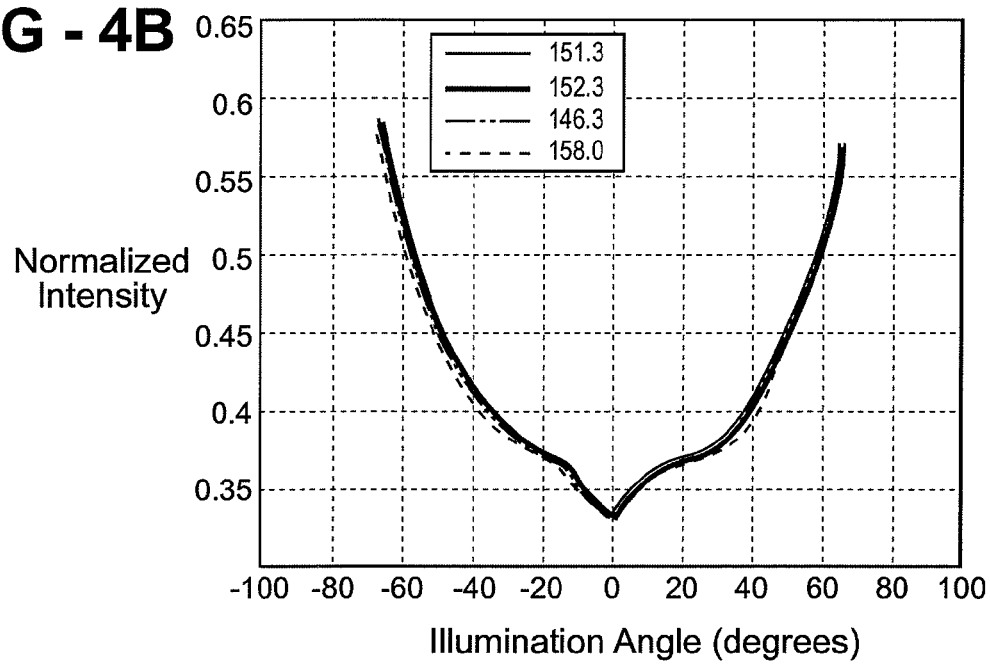
Figure 4C:
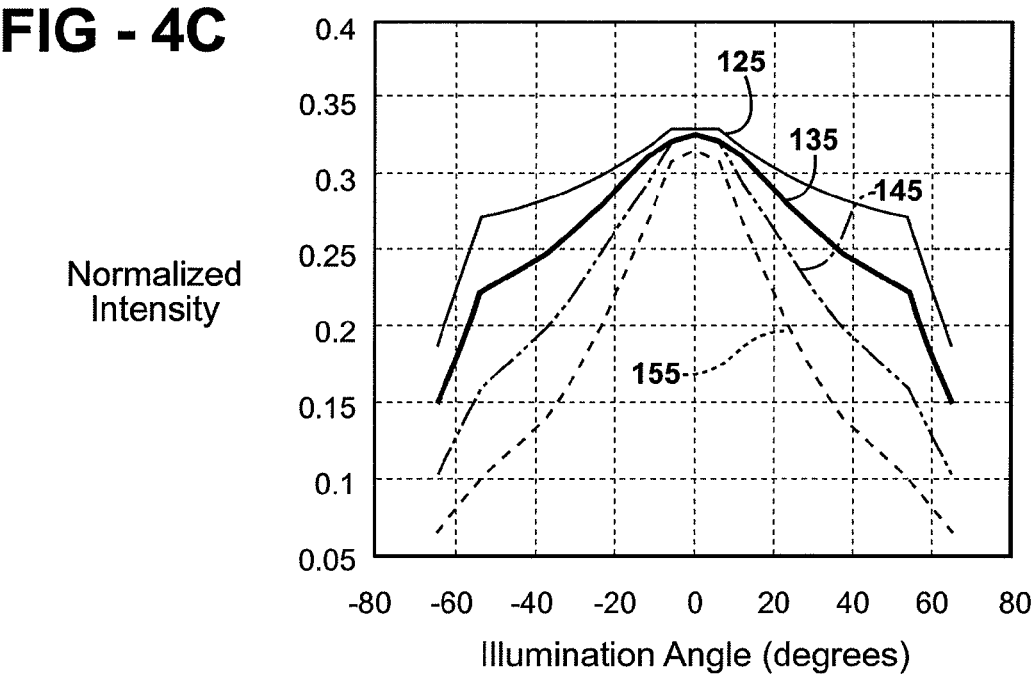

The data shown in FIGS. 4A and 4C are simulation results and the data on in FIGS. 4B and 4D are actual experimental results. The vertical axes in FIGS. 4A-4D are normalized units. The simulations span the range of CD values measured with AFM and SEM. The experimental data are silicon corrected and compare most favorably with the simulations between 145 nm and 155 nm. For the data in FIGS. 4A-4D illumination NA=0.8, collection NA=0.95 and wavelength=546 nm. For the simulation data curves (FIGS. 4A and 4C) the top was 125 nm, the Mid 1 was 135 nm, the Mid 2 was 145 nm and the bottom was 155 nm. For the experimental (SEM) data curves Die 1,1=158 nm, Die −1,0=152.3 nm, Die 0,−1=151.3 nm and Die −1,−1=146.3 nm. During the course of the present invention, higher resolution simulation confirmed the results shown in FIGS. 4A and 4D.

An important extension or embodiment of the present method can be obtained by using finite gratings which only partially fill the field of view. In this implementation or embodiment, the edges of the finite gratings will yield in the typical fashion higher order scattered light which can be collected and have typical higher frequency character associated with an image. However, the portion of the signal or profile between the edge lines will image with zeroeth order content only. By carefully measuring the intensity of the zeroeth order center part of the profile a mapping of the intensity versus wavelength or angle of illumination can be made. Using modeling this can be directly attributed to a specific set of structures as is done in scatterometry.

Alternatively, an empirical approach can be used whereby samples of known feature size or geometry are measured using an alternative reliable measurement and then reference the repeatable measurements using the scanning approach and output signature to the reference data. This empirical approach can be used in several of the implementations described here.

Another aspect of the present invention involves the use of targets that only fill a portion of the imaged field of view. The use of such targets incorporated into or onto the substrate to be imaged allows the substrate to form a self calibration or normalization to monitor and calibrate the intensity. Such calibration or normalization is very important as an intensity-only measurement is very sensitive to lamp fluctuations and details in the optical configuration and alignment which may vary the intensity as a function of time. The use of on-board substrate targets allows monitoring with the background intensity and real time normalization.

Using a full field of view imaging according to the present invention, also allows a window to be placed around that part of the target for mapping and plotting of the intensity as a function of angle or wavelength at a particular part in the field of view. The data captured by a CCD type camera can be binned and analyzed.

An alternative target design here is a more complex structure than an array of lines. As an example, a structure such as a dense memory device can be imaged as a function of illumination angle. The target response may be a combination of zero order and higher order optical information depending on the local pitch, size and geometry. The data from the images as a function of illumination angle can then be binned as just described above and the local signature at a given location in the field of view ascribed to a geometry or geometrical value.

Likewise, multiple targets can be used in a single field of view for measurement or multiple measurements. This allows for a linearity type calibration since a particular range of the measured parameters of interest can be bracketed by those sets of targets. This implementation allows for essentially a large number of parallel, simultaneous scatterometry type measurements using the Scatterfield platform. A complete set of example data and analysis is shown in FIGS. 5A-5C, 6A-6F and 7A-7F.

The targets used to obtain the data in FIGS. 5A-7F consisted of an array of small line arrays on a substrate. These targets are intended to allow measurement of overlay between two layers with a set of targets that can be imaged using the zero order imaging approach of the present invention. The targets investigated during the course of the present invention included outer line sets that were formed from one photolithograph level and an intermediate line set that was formed from a second photo level. The target designs investigated included sets of eight lines with a variety of line lengths, line separation, and line widths to allow investigation of these parameters on target performance. The target designs varied from a single set of eight lines from one level adjacent to a second set of eight lines on a second level to more complex targets with arrays of 3×5 line sets. These more complex targets were designed to allow imaging at two different modes. In the first mode the optical response to individual line sets includes higher-order optical content reflecting from the central part of the lines. In the second mode, which is shown in FIGS. 5A-5C, the targets are imaged in the zero order imaging mode. The normalized intensity is shown along the vertical axis and the position along the targets in nm is shown along the horizontal axis. The upper data plotted in FIGS. 5A-5C is raw data and the lower data is weighted data. In FIGS. 5A-5C only zero-order specular reflection occurs from the central target region of an individual line set although the individual line sets do reflect higher order optical content form their edges. In FIGS. 5A-5C a standard target was used that did not include designed-in CD variation. The nominal features of the target were 50 nm CD with 270 nm pitch.

Figure 6D:
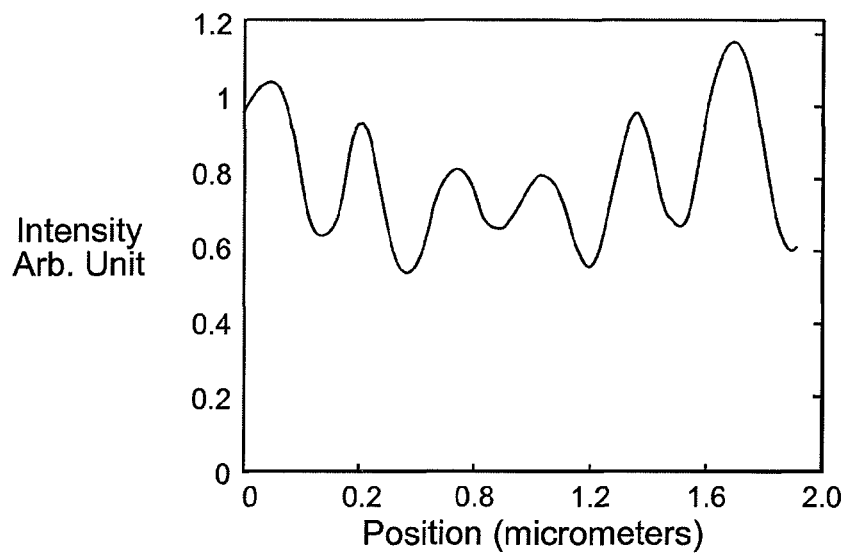
Figure 6E:
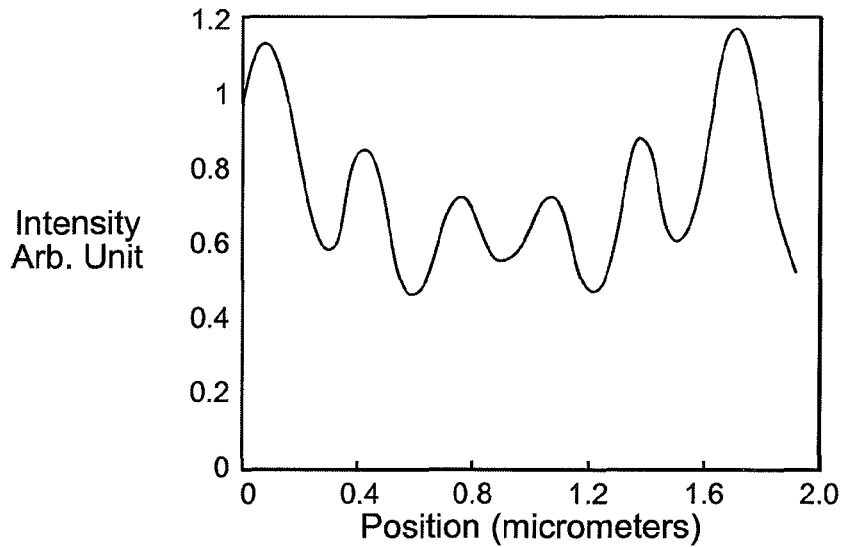
Figure 6F:
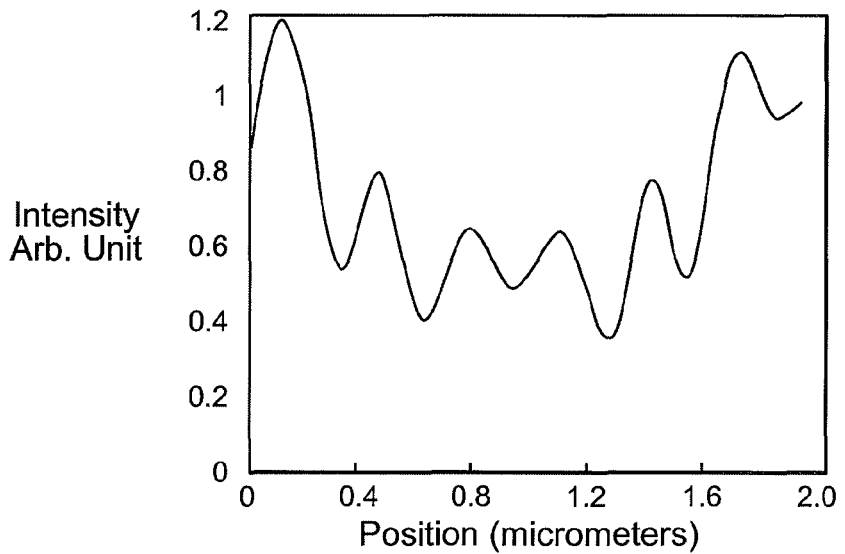

Using full field angle scan targets enable simultaneous analysis of nine line arrays. To enhance this approach and test sensitivity a special high resolution target array was designed which has built in CD variations across the field of view. Each row of line sets in this target has a different design CD. FIGS. 6A-6F show the normal incidence 0° illumination image data which contains profiles for three different design CDs as just described. In these data, the design increments are 5 nm and the average nominal CDs measured by AFM and SEM are 55 nm, 60 nm and 65 nm. From this image an average intensity is determined for the central region for each profile. FIGS. 6A-6C show the theoretical results and FIGS. 6D-6F show the experimental data. From each profile acquired at a given illumination angle an average integrated intensity (AII) value can be determined for the central target region. Both the experimental results and simulation data show approximately 10 percent changes in the AII for each increment in linewidth. These curves are normalized to background and no silicon reflectivity corrections have been applied. The movement of the mean intensity for both theoretical and experimental data are noted. Normal incidence, p-polarized light and linear targets were used.

Figure 7A:
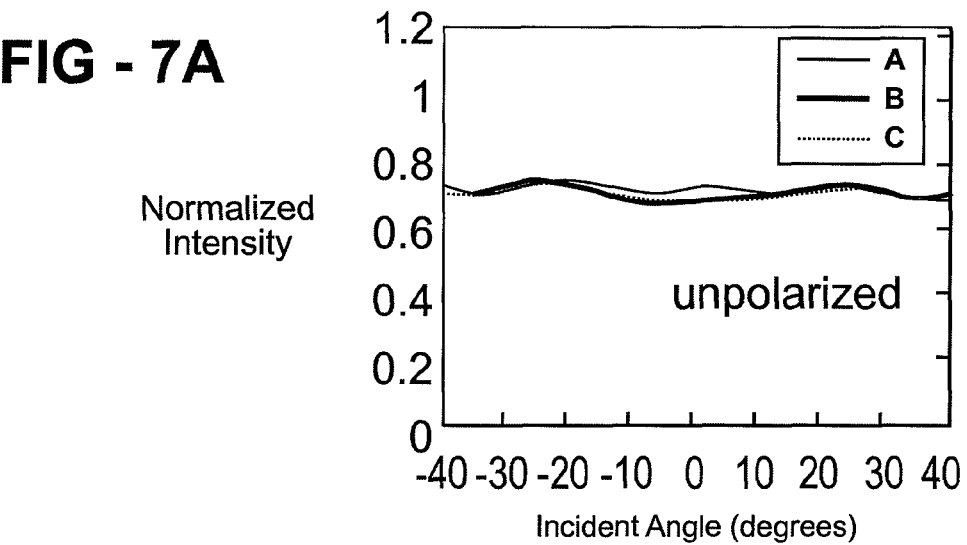
FIGS. 7A-7F are a complete set of angle-resolved data.
Figure 7B:
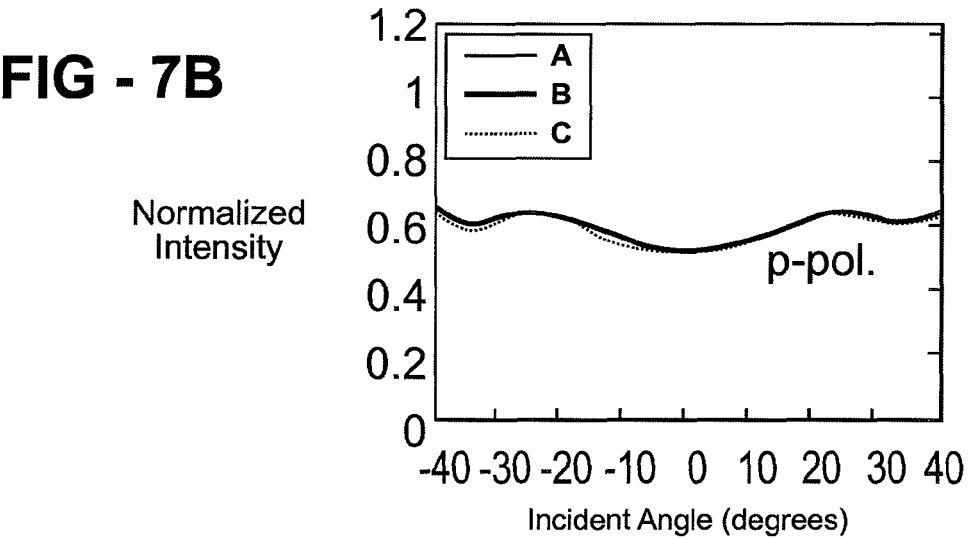
Figure 7C:
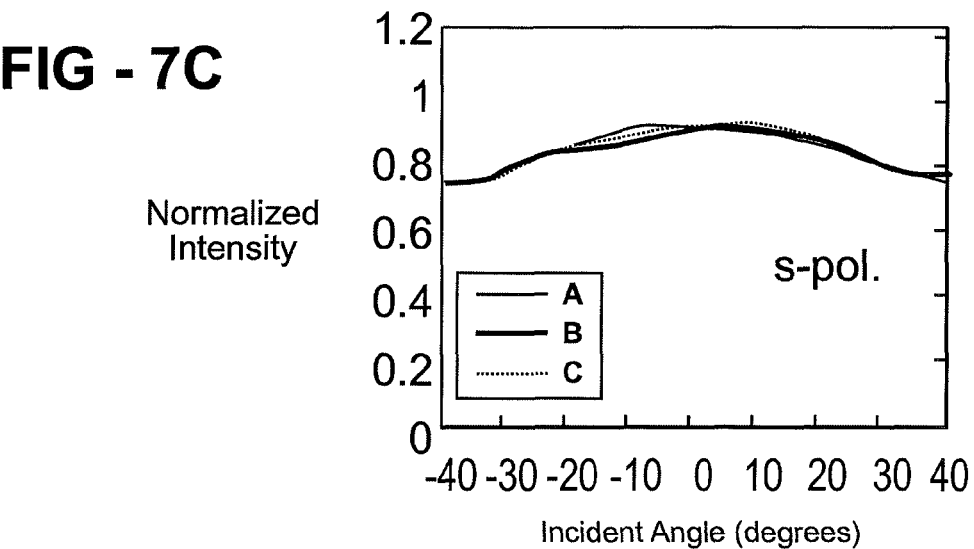
Figure 7D:
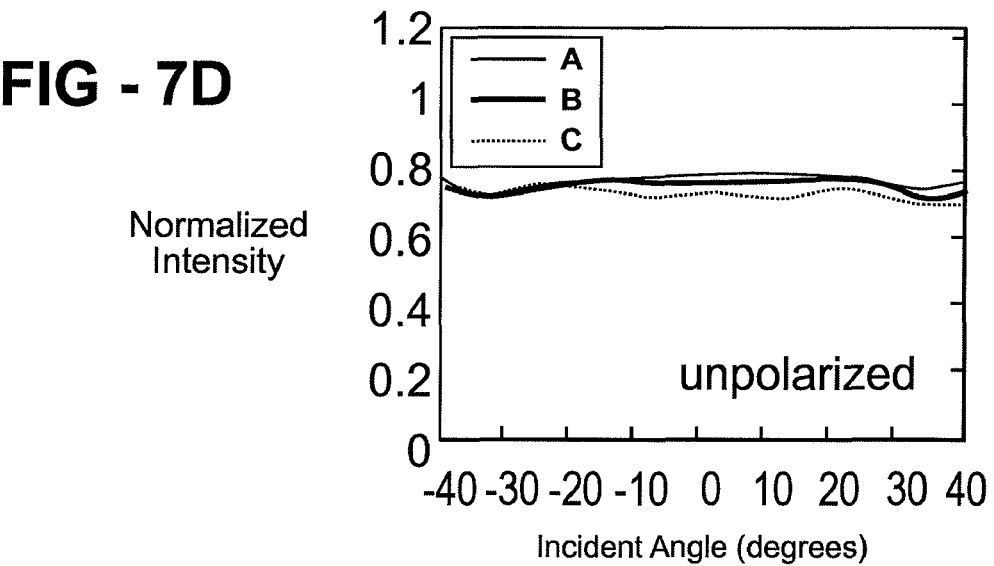
Figure 7E:
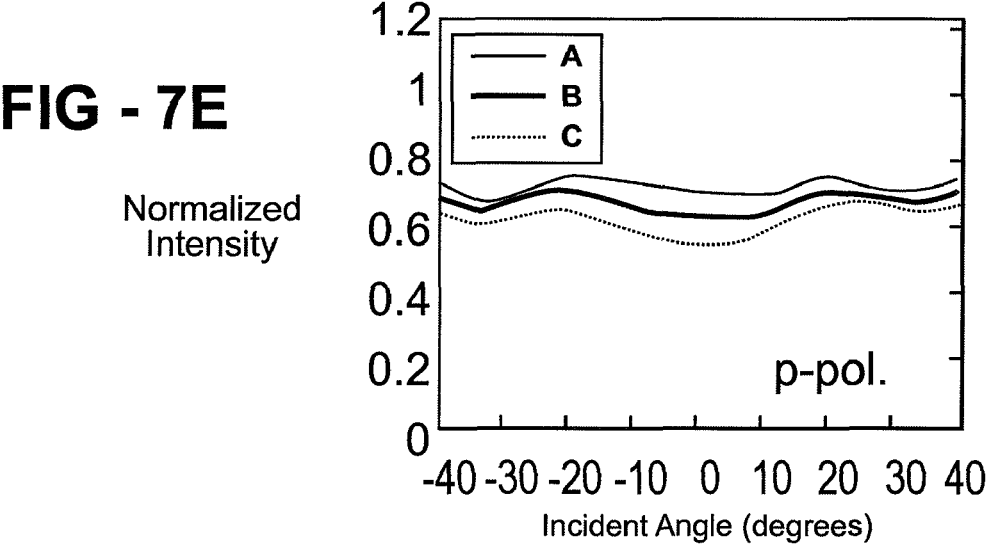
Figure 7F:
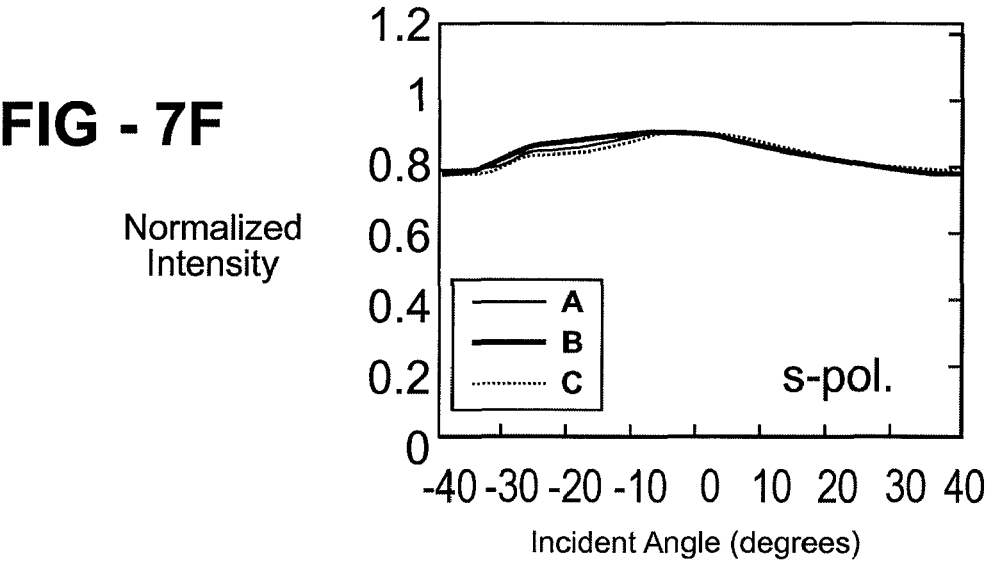

A complete set of angle-resolved data is shown in FIGS. 7A-7F. The data set in FIGS. 7A-7C is for a non-incremental 3×3 overlay target and the data set for FIGS. 7D-7F in for an incremented linearity target. The data set in FIGS. 7A-7C shows no substantial sensitivity to linewidth variations across the target while the data set for FIGS. 7D-7F shows a clear monotomic response to the changes in linewidth across the target. The data from FIGS. 6D-6F are representative of 0° illumination angle from the center of the p-polarized plot. The data clearly indicate the importance of polarization with respect to sensitivity to changes in linewidth. The data in FIGS. 7A-7F are for linear targets and the mean intensity from the central part of each profile can be analyzed for sensitivity to changes in CD.

The zero-order imaging of the present invention can be performed with a scanning stage and a photometer/slit configuration although this presents some additional practical challenges. The basic approach can be realized using one of several methods to scan the illumination as a function of angle or scan wavelength. Alternatively, just using a few fixed angles, or even the on axis illumination and monitoring the average intensity for a given window may enable linewidth to be measured or the measurement of more complex feature geometry.

Figure 8:
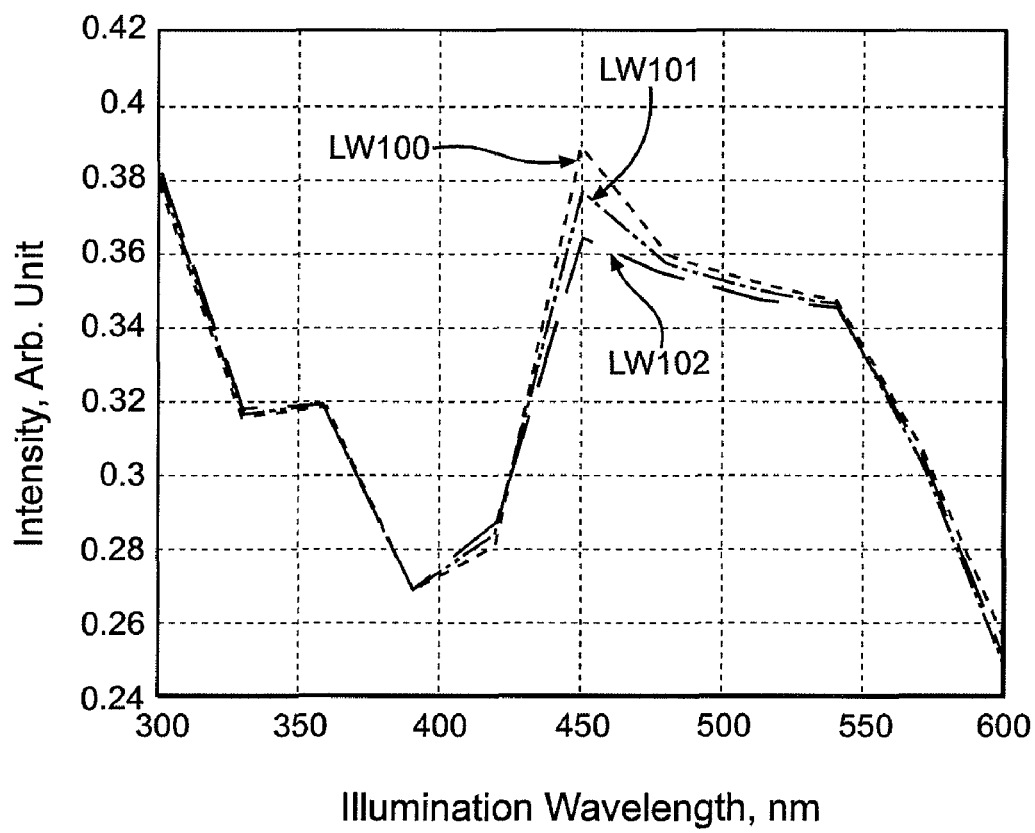
FIG. 8 shows the average integrated image intensity signatures for line arrays with 100, 101 and 102 nm line widths at 0.5 illumination NA, 0.8 collection NA, 100 nm line height and 450 pitch.

FIG. 8 shows the average integrated image intensity signatures for line arrays with 100, 101 and 102 nm line widths at 0.5 illumination NA, 0.8 collection NA, 100 nm line height and 450 pitch. These are examples of a scanned wavelength approach which verifies that the zero-order imaging of the present invention can be performed using one of several methods to scan the illumination as a function of angle or scan wavelength.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and as set forth in the attached claims.

What is claimed is:

1. A method of imaging diffracted light using an optical microscope in a Kohler illuminated system, comprising the steps of:
   a) providing at least one target, an illumination source for illuminating the at least one target, and an aperture disposed at a back focal plane between the at least one target and the illumination source, wherein the illumination source is imaged in the back focal plane;
   b) scanning the aperture in the back focal plane to vary the angle of illumination of the at least one target;
   c) directing light from the illumination source onto the at least one target so as to cause the target to diffract the light, the light directed onto the at least one target approximating plane waves;
   d) collecting at an imaging device, via an objective lens, the diffracted light for each of the varied angles of illumination;
   e) determining structural features of the at least one target from the collected diffracted light by correlating the average intensity of the collected diffracted light for each of the varied angles of illumination to produce an image that corresponds to structural features of the at least one target.

2. The method of claim 1, wherein the imaging device is a CCD camera and the image is a data image.

3. The method of claim 1, wherein in step c) the light is directed over the field of view of the imaging device and the at least one target fills the entire field of view of the imaging device.

4. The method of claim 1, wherein in step c) the light is directed over the field of view of the imaging device and the at least one target fills only a portion of the entire field of view of the imaging device.

5. The method of claim 1, wherein step a) comprises providing a plurality of targets, step c) comprises directing light onto each of the plurality of targets, and step e) comprises determining structural features of each of the plurality of targets.

6. The method of claim 1, wherein step a) comprises providing the target on a substrate, step c) comprises directing light onto both the target and the substrate, and step e) comprises determining structural features of both the target and the substrate.

7. The method of claim 6, wherein the step of determining structural features of both the target and the substrate from the collected diffracted light comprises using the structural features of the target as a calibration or normalized reference for determining the structural features of the substrate.

8. The method of claim 6, wherein step a) comprises providing a plurality of targets on a substrate, step c) comprises directing light onto both the plurality of targets and the substrate, and step e) comprises determining structural features of both the plurality of targets and the substrate.

9. The method of claim 6, wherein, in the step of providing a target on a substrate, the target is fabricated on the substrate.

10. The method of claim 6, wherein, in the step of providing a target on a substrate, the target is fabricated separately from and provided on the substrate.

11. The method of claim 1, wherein, in the step of providing a target, the target comprises a semiconductor device.

* * * * *